United States Patent [19]

Campbell et al.

[11] Patent Number: 4,743,480
[45] Date of Patent: May 10, 1988

[54] APPARATUS AND METHOD FOR EXTRUDING AND EXPANDING POLYTETRAFLUOROETHYLENE TUBING AND THE PRODUCTS PRODUCED THEREBY

[75] Inventors: Michael L. Campbell; Benjamin G. Williams; Rob G. Riffle; Charles E. Biggerstaff, all of Flagstaff, Ariz.

[73] Assignee: W. L. Gore & Associates, Inc., Newark, Del.

[21] Appl. No.: 930,411

[22] Filed: Nov. 13, 1986

[51] Int. Cl.⁴ .............................................. D02G 3/00
[52] U.S. Cl. ...................................... 428/36; 428/422; 623/1; 138/177; 138/DIG. 3; 264/288.8
[58] Field of Search ................. 264/127, 288.8; 623/1; 128/DIG. 14; 138/177, DIG. 3; 428/36, 422

[56] References Cited

U.S. PATENT DOCUMENTS

| | | | |
|---|---|---|---|
| 3,008,187 | 11/1961 | Slade | 264/127 |
| 3,953,566 | 4/1976 | Gore | 264/154 |
| 4,082,893 | 4/1978 | Okita | 428/422 |
| 4,187,390 | 2/1980 | Gore | 428/36 |
| 4,277,429 | 7/1981 | Okita | 264/127 |
| 4,279,245 | 7/1981 | Takagi et al. | 128/DIG. 14 |
| 4,478,665 | 10/1984 | Hugis | 264/127 |
| 4,482,516 | 11/1984 | Bowman et al. | 264/288.8 |

Primary Examiner—Richard R. Bueker
Assistant Examiner—James J. Seidleck
Attorney, Agent, or Firm—Mortenson & Uebler

[57] ABSTRACT

Apparatus, a method for extruding and expanding tubular products of polytetrafluoroethylene (PTFE) and the products produced thereby are provided. In the apparatus, at least one helical groove is placed in the wall of the extruder tip or die. Preferably, at least one groove is machined in the tip having a pitch angle of 45 degrees and at least one groove is machined in the die having a pitch opposite that (135 degrees) of the tip groove. In the expanded products produced according to the invention, at at least one radial position within the wall of a tube substantially all of the longitudinal axes of the nodes are oriented at an angle between about 85 degrees and about 15 degrees with respect to the longitudinal axis of the tube. In a preferred embodiment, substantially all of the longitudinal axes of the nodes located adjacent the inside wall of the tube are oriented at an angle between about 85 degrees and about 15 degrees with respect to the longitudinal axis of the tube, and substantially all of the longitudinal axes of the nodes which are located adjacent the outside wall of the tube are oriented at an angle between about 15 degrees and about 165 degrees with respect to the longitudinal axis of the tube. For the preferred product, its hoop strength is increased over an otherwise identical tube extruded using smooth surfaced, nongrooved extrusion tip and die.

22 Claims, 3 Drawing Sheets

Direction Of Uniaxial Expansion

Direction Of Uniaxial Expansion    Direction Of Uniaxial Expansion

Direction Of Uniaxial Expansion
Helix Angle: 45°

I.D.-O.D. HELIX

Direction Of Uniaxial Expansion
Helix Angle: 135°

Direction Of Uniaxial Expansion
Helix Angle: 75°

APPARATUS AND METHOD FOR EXTRUDING AND EXPANDING POLYTETRAFLUOROETHYLENE TUBING AND THE PRODUCTS PRODUCED THEREBY

BACKGROUND OF THE INVENTION

1. Field of the Invention

This invention relates to the extrusion of polytetrafluoroethylene (PTFE) tubing utilizing, in combination, a helically grooved extrusion tip and/or a helically grooved extrusion die. Such tubing, after removal of lubricant extrusion aid, can be expanded by stretching to produce an expanded, porous PTFE product having an angular orientation of the node and fibril microstructure. Products having increased strength compared to conventionally extruded and expanded tubes can be produced. Articles made by this process and apparatus are particularly suitable for use in the medical field, but they also have uses in nonmedical fields.

2. Description of the Prior Art

The products of this invention derive from paste-formed, extruded tubular products of PTFE. Paste extrusion or paste forming techniques are well known and consist of mixing a coagulated dispersion of PTFE resin with a liquid lubricant, preforming a tubular billet thereof, and forcing the mixture through an annular extrusion orifice in a ram-type batch extruder to form a coherent, extruded, unsintered PTFE tube. The lubricant is then removed, usually by a heat drying process, to form a porous, unsintered PTFE tube having a density usually within the range of 1.5 to 1.7 gm/cc. Such densities correspond to porosities of approximately 39% to 26%, respectively. The unsintered tube can be heated to a temperature above its crystalline melt point of about 345° C. to sinter it thereby coalescing the porous material to form a nonporous, sintered PTFE tube.

U.S. Pat. No. 3,008,187, discloses a method of forming PTFE tubing having improved resistance to cracking and seepage of low viscosity fluids. That method consists of extruding a preformed, annular billet of a mixture of PTFE resin and a volatile extrusion aid through an extruder barrel provided with a centrally located mandrel, through a circular, tapered entry region and thence through an annular orifice to form a tube. Both a portion of the tapered circular inner surface of the tapered entry region and the tapered circular outer surface of the mandrel within the entry region are provided with a plurality of helical grooves. The grooves displace the fibers of tetrafluoroethylene resin formed at the outer surface layer and the inner surface layer within the tapered entrance region.

U.S. Pat. No. 3,953,566 discloses and claims a process for making porous, expanded PTFE and U.S. Pat. No. 4,187,390 discloses and claims products of porous, expanded PTFE. The microstructure of those porous, uniaxially expanded PTFE products comprises nodes interconnected by fibrils in which the long axis of the nodes are oriented substantially perpendicularly to the direction of uniaxial expansion.

The products of U.S. Pat. No. 4,187,390 have high matrix tensile strengths, specifically, above 7,300 psi in at least one direction. Both U.S. Pat. No. 3,953,566 and U.S. Pat. No. 4,187,390 are incorporated herein by reference thereto.

SUMMARY OF THE INVENTION

An extruded and expanded tube of a porous material consisting essentially of highly crystalline PTFE is provided, the tube having a longitudinal axis and tube wall having an inside radius and an outside radius, which PTFE material has a microstructure characterized by elongated nodes, each node having a longitudinal axis and a transverse axis, which nodes are interconnected by fine fibrils, substantially all of the longitudinal axes of the nodes at at least one radial position within the tube wall being oriented at an angle between about 85 degrees and about 15 degrees with respect to the longitudinal axis of the tube. Such tube which has not been heated to a temperature above its crystalline melt point has a crystallinity greater than about 95% and one which has been heated to a temperature above the crystalline melt point of PTFE has a crystallinity below about 95%. Preferably, substantially all of the longitudinal axes of the nodes which are located adjacent the inside radius of the tube are oriented at an angle between about 85 degrees and about 15 degrees with respect to the longitudinal axis of the tube, and substantially all of the longitudinal axes of the nodes which are located adjacent the outside radius of the tube are oriented at an angle between about 15 degrees and about 165 degrees with respect to the longitudinal axis of the tube. The tube of the invention which has not been heated above its crystalline melt point may have a matrix tensile strength in at least one direction above about 7,300 psi. The tube which has been heated above its crystalline melt point may have a matrix tensile strength in at least one direction above about 7,300 psi. The tube may be slit longitudinally thereby forming a sheet. The sheet may be further rolled down. The tube may be rolled down without slitting thereby forming a sheet. Preferably, substantially all of the longitudinal axes of the nodes at at least one radial position within the tube wall are oriented at an angle of about 30 degrees to about 60 degrees with respect to the longitudinal axis of the tube and, most preferably, substantially all of the longitudinal axes of the nodes which are located adjacent the inside radius of the tube are oriented at an angle of about 30 degrees to about 60 degrees with respect to the longitudinal axes of the tube, and substantially all of the longitudinal axes of the nodes which are located adjacent the outside radius of the tube are oriented at an angle of about 30 degrees to about 150 degrees with respect to the longitudinal axis of said tube.

Apparatus for extruding tubing of PTFE is provided comprising, in combination, a hollow, cylindrical barrel containing a mandrel centrally positioned within the barrel, the barrel having a resin supply region, a tapered region leading from the supply region to an annular outflow region comprising an external, hollow, circular cylindrical die having positioned centrally therein the circularly cylindrical tip of the mandrel, the tip and die forming an annulus, at least one of the tip and die having at least one groove in the surface thereof, the groove being oriented helically with respect to the longitudinal axis of the tip and die, the apparatus including a ram capable of reciprocation within the barrel and surrounding the mandrel, and means for providing the ram with reciprocating movement whereby, when a preformed, tubular billet of lubricated PTFE is placed in the barrel and the ram is activated to force the PTFE through the annulus, tubing is provided having at least one helically oriented ridge on at least one surface thereof. Both the tip and the die may have at least one groove in the surface thereof, the grooves being oriented helically with respect to the longitudinal axis of the tip and die. The tip preferably has at least one groove in the surface thereof pitched at an angle between about 15 degrees and about 85 degrees with respect to the longitudinal axis of the tip or at an angle between about 95 degrees and about 165 degrees with respect to the longitudinal axis of the tip. The die preferably has at least one groove in the surface thereof pitched at an angle between about 15 degrees and about 85 degrees with respect to the longitudinal axis of the die or at an angle between about 95 degrees and about 165 degrees with respect to the longitudinal axis of the die. The groove in the tip is preferably of opposite pitch to the groove in the die. The groove in the tip most preferably has a pitch angle of 45 degrees or of 135 degrees. A groove in either the tip or the die can be formed by milling the groove into the surface of the tooling or by adding materials to the surface thereby forming ridges which would define grooves between them, or by other means that would form grooves on the surface of the tip and die. In one embodiment, the tip has at least one groove in the surface thereof which gradually decreases in depth longitudinally along the tip, the depth approaching zero at the exit end of the annulus between the tip and the die, whereby an extruded tube exiting the apparatus has a smooth-surfaced inner bore. The apparatus may include means for applying pressure to the external surface of the tubing thereby smoothing its surface and substantially eliminating any ridges therein. The means for applying pressure can be roller means applied while the tubing is held on a mandrel extending through its bore, or by other means such as additions to or modifications to the extruder tooling that would smooth the outer surface of the tube.

A process for extrusion of PTFE tubing is also provided comprising extruding a preformed billet of a mixture of coagulated dispersion of PTFE and liquid lubricant through an extruder comprising a hollow, cylindrical barrel containing a mandrel centrally positioned within the barrel, the barrel having a resin supply region, a tapered region leading from the supply region to an annular outflow region comprising an external, hollow, circular cylindrical die having positioned centrally therein the circularly cylindrical tip of the mandrel, the tip and die forming an annulus, at least one of the tip and die having at least one groove in the surface thereof, the groove being oriented helically with respect to the longitudinal axis of the tip and die, the apparatus including a ram capable of reciprocation within the barrel and surrounding the mandrel, forcing the PTFE through the annulus, thereby producing extruded, unsintered tubing having at least one helically oriented ridge on at least one surface thereof. The process may include applying pressure to the external surface of the extruded tubing thereby smoothing its surface and substantially eliminating any ridges therein. The pressure may be applied by roller means rolling over the external surface of the extruded tubing while the tubing is held on a mandrel extending through the bore of the tubing. The process may include expanding the extruded tubing, after removal of liquid lubricant, by stretching the unsintered tubing preferably at a rate exceeding about 10% per second and maintaining the tubing at a temperature between about 35° C. and the crystalline melt point of the PTFE during the stretching. The rate of stretch may exceed about 100% per second and the tubing may be expanded such that its final length in the direction of expansion is greater than about four times the original length. The final length may be greater than about seven times the original length. The stretched tube may be heated to a temperature above the crystalline melting temperature of PTFE. The process may include the subsequent step of slitting the stretched tubing along its length thereby producing a sheet of expanded PTFE. The sheet may be further rolled down. The tubing may be rolled down without slitting producing a sheet of expanded PTFE.

DETAILED DESCRIPTION OF THE INVENTION AND PREFERRED EMBODIMENTS WITH REFERENCE TO THE DRAWINGS

Apparatus and a method for extruding and expanding tubular products of polytetrafluoroethylene (PTFE) are provided. The apparatus is distinct from prior apparatus by virtue of at least one helical groove being placed in the wall of the extruder tip or die. Preferably, at least one groove is machined in the tip having a pitch angle of 45 degrees and at least one groove is machined in the die having a pitch angle opposite that of the tip groove. The expanded products produced according to the invention are distinct from prior expanded PTFE products in that, at at least one radial position within the wall of a tube, substantially all of the longitudinal axes of the nodes are oriented at an angle between about 85 degrees and about 15 degrees with respect to the longitudinal axis of the tube. In a preferred embodiment, substantially all of the longitudinal axes of the nodes located adjacent the inside wall of the tube are oriented at an angle between about 85 degrees and about 15 degrees with respect to the longitudinal axis of the tube, and substantially all of the longitudinal axes of the nodes which are located adjacent the outside wall of the tube are oriented at an angle between about 15 degrees and about 165 degrees with respect to the longitudinal axis of the tube. For the preferred product, its hoop strength is increased over an otherwise identical tube extruded using smooth-surfaced, nongrooved extrusion tip and die.

Figure 1:
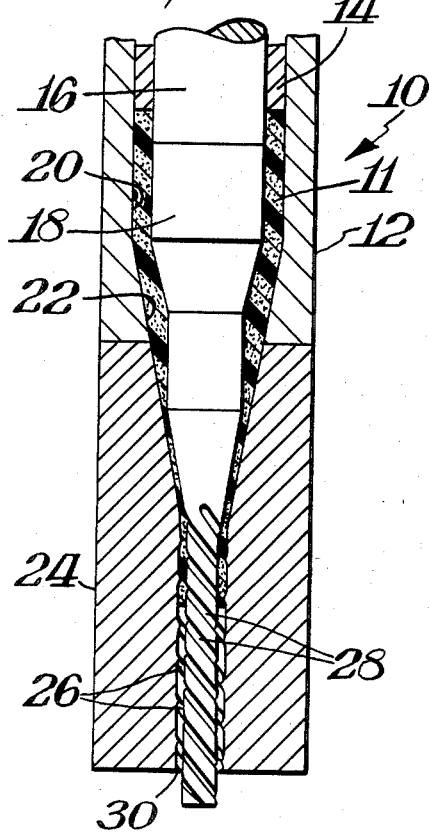
FIG. 1 is a schematic representation of a portion of an extruder for extruding tubes of PTFE, the extruder having helically grooved mandrel tip and die.

A detailed description of the invention is best provided with reference to the drawings wherein FIG. 1 is a schematic representation of a portion of an extruder for extruding tubes of PTFE. Paste extrusion of PTFE consists of mixing the PTFE resin with a liquid lubricant, preforming a tubular billet and forcing the mixture through an annular orifice substantially as shown in FIG. 1. Therein, extrusion apparatus 10 comprises a cylindrical barrel 12 containing a mandrel 16 centrally positioned within barrel 12 and having a tip section 18 as shown. The annular orifice 30 through which the tube is extruded is formed by the tip 18 and the die 24 attached to the end of barrel 12. Ram 14 forces the PTFE/lubricant billet 11 through barrel 12 having inside wall 20, thence through the tapered entry region having inside wall 22, and thence through the annular region 30 formed by tip 18 and die 24. In FIG. 1 both tip 18 and die 24 have helically oriented grooves in their respective outer and inner surfaces, pitched in opposite directions. Tubes extruded through orifice 30 have corresponding ridges in their inner and outer tube walls.

Figure 2:
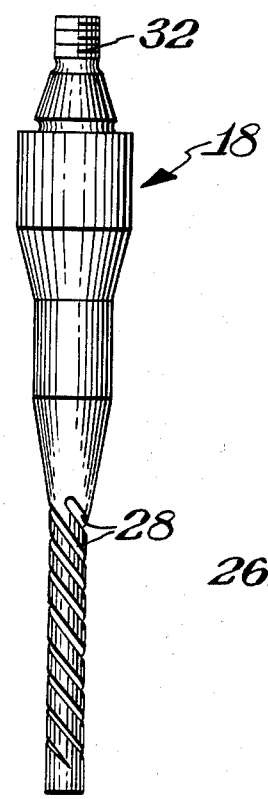
FIG. 2 is an elevational view of a helically grooved mandrel tip according to the invention.

FIG. 2 is an elevational view of tip 18 having thread means 32 for affixing the tip 18 to mandrel 16 shown in FIG. 1. A helical groove 28, having a pitch angle of 45 degrees, is shown in FIG. 2. A plurality of such grooves may be employed. The groove 28 gradually diminishes in depth as it approaches the tip's exit end. A tube extruded with such a tip has a smooth-surfaced inside wall.

Figure 3:
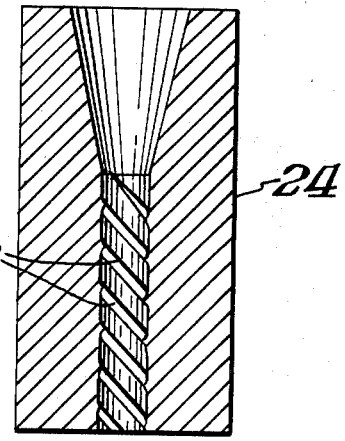
FIGS. 3 and 4 are cross-sectional views of alternate embodiments of helically grooved dies according to the invention.

FIG. 3 is a cross-sectional view of the die 24 shown in FIG. 1. This has a groove 26 oriented in the opposite direction as the groove 28 in the tip 18 shown in FIG. 2. As with the tip, multiple grooves may be employed in the die.

Figure 4:
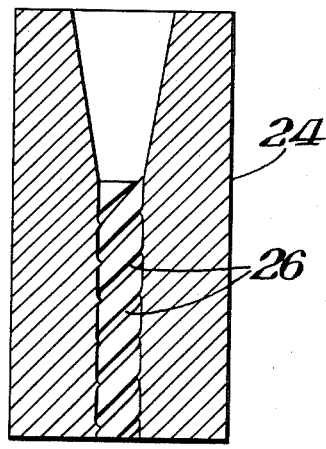

FIG. 4 is a cross-sectional view of a die 24 having a groove 26 oriented such that its pitch angle is oriented in the same direction as that of groove 28 in the tip 18 shown in FIG. 2.

Figure 5:
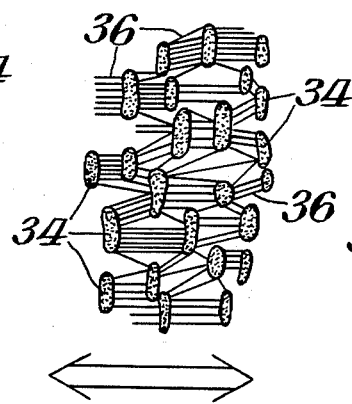
FIG. 5 is a schematic plan view of a section of expanded PTFE known in the prior art as seen under a microscope which was extruded prior to expansion using smooth-surfaced extrusion tip and die.

FIG. 5 is a schematic plan view of a section of a uniaxially expanded PTFE produced by the techniques disclosed in U.S. Pat. No. 3,953,566, incorporated herein by reference. The section is depicted as seen under a microscope possessing many nodes 34 interconnected by many fine fibrils 36. This microstructure, in which the longitudinal axes of the nodes 34 are all substantially perpendicular to the longitudinal axis of the tube (the direction of uniaxial expansion), results when tubing is extruded prior to expansion using smooth surfaced tip and die.

Figure 6:
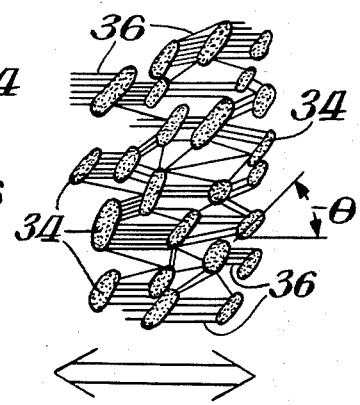
FIG. 6 is a schematic plan view of a section of expanded PTFE as seen under a microscope which was extruded prior to expansion using the helically grooved extrusion tip and die according to the invention.

FIG. 6 is a schematic plan view of a section of expanded PTFE as seen under a microscope which was extruded prior to expansion using the helically grooved extrusion tip and/or die according to the invention. Therein, nodes 34 are interconnected by fibrils 36 but the longitudinal axes of substantially all nodes 34 are oriented at an angle $\theta$ to the direction of uniaxial expansion which is the longitudinal axis of the tube. Depending on the pitch angle of the grooves, $\theta$ may vary between about 85 degrees and about about 15 degrees.

Figure 7:
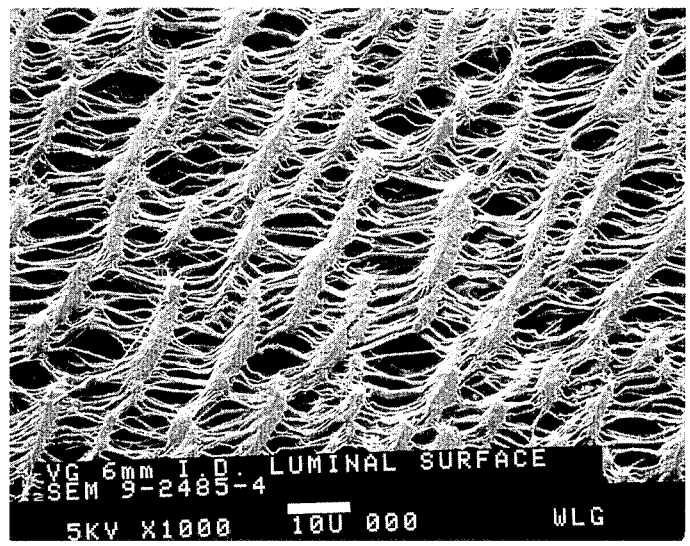
FIGS. 7, 8 and 9 are photomicrographs showing the node-fibril orientation of a product according to the invention.

FIG. 7 is a photomicrograph taken at 1000X magnification of the inside wall (lumen) of a PTFE tube extruded and expanded according to the invention. The longitudinal axes of substantially all nodes are oriented at an angle of approximately 60 degrees with respect to the longitudinal axis of the tube. The angle of pitch of the grooves in the tip used in extrusion is indicated to be 45 degrees.

Figure 8:
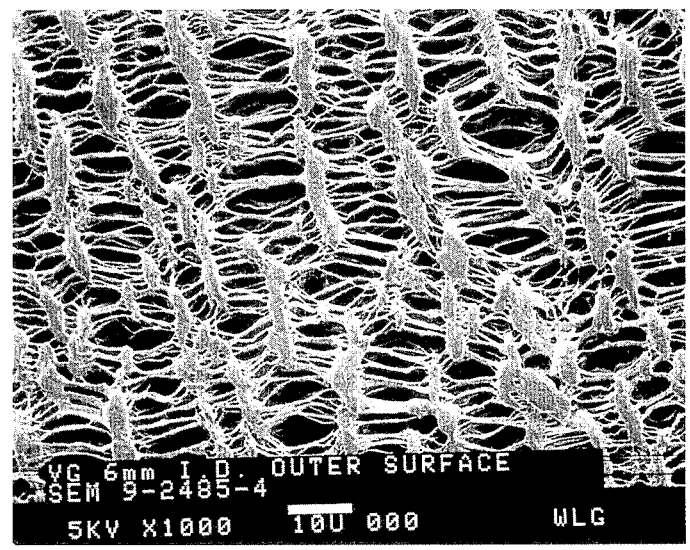

FIG. 8 is a photomicrograph taken at 1000X magnification of the outside wall of the extruded and expanded tube according to the invention. The longitudinal axes of substantially all nodes are oriented at an angle of approximately 60 degrees* with respect to the longitudinal axis of the tube. The angle of pitch of the grooves in the die used in extrusion was opposite that of the grooves in the tip, i.e. the angle of pitch of the die grooves was 135 degrees with respect to the longitudinal axis of the tube. The relationship between the orientation of the nodes at the inside wall of the tubes and at the outside wall after expansion is not completely understood. What is believed is that, if the longitudinal axes of the nodes at the inside wall are oriented at an angle between about 85 degrees and about 15 degrees with respect to the longitudinal axis of the tube, the longitudinal axes of substantially all nodes near the external surface of the tube may vary between about 15 degrees and about 165 degrees, depending upon many variables other than but including the helical angles of the grooves in the tip and die.

*The tube was slit and viewed flat for both inside and outside wall surfaces. The inside wall of the specimen was photographed and the specimen then was turned over and the outside wall photographed. Thus, while the nodes in FIG. 8 appear to be oriented at 120 degrees, because of the specimen inversion, they are actually oriented at 60 degrees.

Figure 9:
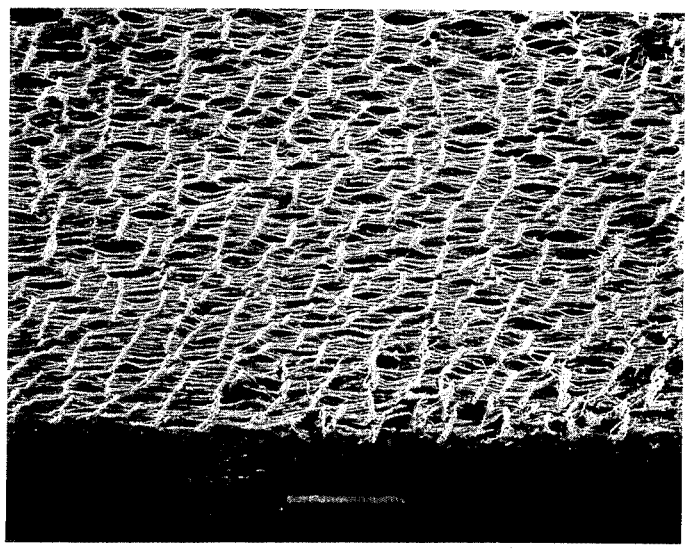

FIG. 9 is a photomicrograph taken at 200x magnification of the inside wall of a PTFE tube extruded and expanded according to the invention. The longitudinal axes of substantially all nodes are oriented at an angle of approximately 60 degrees with respect to the longitudinal axis of the tube. The angle of pitch in the single groove in the die used in extrusion was 75 degrees.

According to the invention, the tip and die may have more or less than four helical grooves and the angles of the grooves may vary. Preferably the grooves in the tip run in a direction that is opposite to the direction of the grooves in the die.

An optional step prior to expansion and within the scope of the invention may include the removal of the external ridges on the outside wall of the extruded tube. This can be accomplished by placing the extrudate on a mandrel, mounting the mandrel on a lathe, and at low revolutions applying pressure to the outside surface of the spinning tube with a smooth rod. Other means such as additions to or modifications to the extruder tooling that would smooth the outer surface of the tube may also be used. By using this optional step prior to expansion, the resulting tubes after expansion appear as smooth on their outer surface as tubes extruded with smooth-surfaced tip and die, after expansion. The examples which follow demonstrate that, for otherwise identical processing conditions, the extrusion of PTFE tubes using helically grooved tip and die produces articles which are generally stronger than tubes extruded using smooth-surfaced tip and die. Final products using these techniques may include articles such as film, tubes, and continuous filaments.

Expanded PTFE tubes have found use as artificial vascular grafts. These grafts must have a certain minimum hoop strength. These grafts are often wrapped with an outer reinforcement in order to achieve the desired strength. Tubes of the present invention may have sufficient strength for this use without the need for a reinforcement.

The examples below include comparisons of strengths of tubes made by conventional methods and those made according to the present invention. Test parameters included matrix tensile strength, burst pressure, hoop stress, water entry pressure, suture retention, fibril length and wall thickness. To compute matrix tensile strength of a porous specimen, one divides the maximum force required to break the sample by the cross-sectional area of the porous sample, and then multiplies this quantity by the ratio of the specific gravity of the solid polymer divided by the specific gravity of the porous specimen. Test results are reported at 23° C.

To compute burst pressure one increases the internal water pressure at a fixed rate of about 10 psi/sec. until the test specimen dilitates sufficiently that a 10 psi decrease in internal pressure is detected. The final water pressure at which this phenomenon occurs is the burst pressure. The specimen may or may not actually break during the test. Test results are reported at 23° C.

To compute hoop stress ($\sigma$) on the internal surface of the tube, one uses the burst pressure (p), the internal radius of the tube (a), and the external radius of the tube (b) in the following equation:

$$\sigma_\theta = a^2 p / b^2 - a^2(1 + b^2/a^2)$$

(Reference: *Theory of Elasticity*, S. P. Timoshenko and J. N. Goodier, Engineering Society Monographs, 1970, pp. 65–71.

To compute water entry pressure one subjects a test sample to an incrementally increasing internal water pressure of about 0.2 psi/min. until small beads of water appear on the outer surface of the tube. The water pressure required to do this is the water entry pressure.

To compute suture retention, for use of tubes as vascular grafts, one determines suture holding strength in both the longitudinal and transverse directions. To compute suture retention in the longitudinal direction, a 1200 denier filament is threaded through both tube walls approximately 1 mm from the end of the sample tube. The sample is then installed in a tensile testing apparatus and tested to destruction. The maximum force required to pull the filament from the sample is recorded. To compute suture holding retention in the transverse direction the tube is cut longitudinally and the 1200 denier filament is threaded through one wall approximately 1 mm from the cut edge. Similar tensile testing procedures to those described above are again applied to test destruction in the transverse direction.

To compute fibril length one cuts a sample tube lengthwise and photographs the surface under sufficient magnification. Sufficient fibril lengths are measured from the sample to compute a statistically significant mean fibril length. A fibril length is measured from the edge of one node to the edge of an adjacent node. Fibril lengths less than five microns are not recorded because of indistinct nodal separation.

To compute wall thickness one substracts the inner diameter measurement from the outer diameter measurement and divides by two.

The following examples which disclose processes and products according to the present invention are illustrative only and are not intended to limit the scope of the present invention in any way.

EXAMPLE 1

Expansion Of Tube: Die With One Helical Groove

PTFE resin (Fluon CD-123 obtained from ICI Americas) was blended with 121 cc of "Isopar M" odorless solvent (produced by Exxon Corporation) per pound of PTFE, compressed into a tubular billet, heated to 60° C. and extruded into a 6 mm I. D. and 7.7 mm O. D. tube in a ram extruder having a reduction ratio of about 123:1 in cross-sectional area from billet to the extruded tube. The extruder tooling consisted of a smooth surfaced tip and a die having a single helical groove machined into it a pitch angle of 75° with respect to the longitudinal axis of the die with a right hand twist. The depth of the groove was 0.51 mm. After removal of lubricant, the extruded tube was used to produce a cylindrical tube of porous, expanded, amorphously locked PTFE having a 6 mm internal diameter and outside diameter of 7.7 mm by the process described in U.S. Pat. No. 3,953,566. The stretch conditions were:

Temperature: approximately 300° C.
Stretch Ratio: 7.4:1 (640% increase in length)
Stretching Rate: approximately 105%/sec. (determined by dividing the percent change in length by the duration of the stretching operation)

The stretched tube was then restrained from shrinking and heated in an oven set at approximately 390° C. for a total of about 7 minutes thereby sintering the tube. This heating step can be performed in a single operation or in multiple stages. FIG. 9 is a photomicrograph of the inner surface of this tube. The longitudinal axes of the nodes are angled at approximately 60 degrees with respect to the direction of uniaxial expansion.

EXAMPLE 2

Expansion Of Tube: Tip And Die With Four Helical Grooves Used Separately And In Combination PTFE resin (Fluon CD-123 obtained from ICI Americas) was blended with 121 cc of "Isopar M" odorless solvent (produced by Exxon Corporation) per pound of PTFE, compressed into a tubular billet, heated to 40° C. and extruded into a 6 mm I. D. tube in a ram extruder having a reduction ratio of about 123:1 in cross-sectional area from billet to the extruded tube. Five combinations of extruder tooling were used, chosen from two different dies and three different tips:

1. a smooth surfaced tip and smooth surfaced die.
2. a smooth surfaced tip and a die having four helical grooves machined into it at a pitch angle of 45 degrees (a right hand twist).
3. a tip with four helical grooves machined into it at an angle of 135 degrees (a left hand twist) and a smooth surfaced die,
4. a tip as in #3 and a die as in #2, that is, opposite twist,
5. a tip with four helical grooves machined into it at an angle of 45 degrees (a right hand twist) and a die as in #2, that is, the grooves are pitched in the same direction.

The continuous depth of grooves in the die was 0.51 mm. The grooving in the tips gradually tapered from this depth at the upstream end to zero depth at the exit end of the tip. This produced tubes with smooth inside walls. The external surface of tubes made with grooved dies had ridges.

The extruded tubing from the various tooling combinations were then processed into cylindrical tubes of porous, expanded, amorphously locked PTFE having an approximate internal diameter of 6 mm by the process described in U.S. Pat. No. 3,953,566. The stretch conditions were:

Temperature: approximately 300° C.
Stretch Ratio: 5:1 (400% increase in length)
Stretching Rate: approximately 400%/sec. (determined by dividing the percent change in length by the duration of the stretching operation).

The stretched tubes were then restrained from shrinking and heated in an oven set at approximately 390° C.

for a total of about seven minutes thereby sintering the tube. This heating step can be performed in a single operation or in multiple stages.

A comparison was made between certain physical properties of tubes made with the various combinations of tooling mentioned above. The results are shown in Table 1. These are mean data calculated from five tube samples from each type of extrusion tooling employed.

Stretching Rate: approximately 400%/sec. (determined by dividing the percent change in length by the duration of the stretching operation).

The stretched tube was not amorphously locked, i.e., the PTFE was in an unsintered state.

Four such tubes with a mean inner diameter of 4.2 mm and a mean outer diameter of 5.5 mm were tested to determine longitudinal matrix tensile strength. The mean value was 13852 psi. The testing was done with

TABLE 1

Comparison Of Physical Properties

| Type Of Extrusion Tooling | Internal Diameter (mm) | Wall Thickness (mm) | Suture Retention Longitudinal (g) | Suture Retention Transverse (g) | Water Entry Pressure (psi) | Burst Pressure (psi) | Hoop Stress (psi) | Mean Fibril Length (microns) | Longitudinal Matrix Tensile Strength* (psi) |
| --- | --- | --- | --- | --- | --- | --- | --- | --- | --- |
| 1. Both Smooth | 6.1 | 0.78 | 366 | 828 | 5.6 | 46.0 | 205.5 | 18 | 11282 |
| 2. Smooth Tip, Grooved Die | 6.4 | 0.73 | 498 | 1073 | 6.0 | 51.6 | 254.5 | 18 | 11661 |
| 3. Grooved Tip, Smooth Die | 6.1 | 0.70 | 293 | 926 | 7.1 | 55.1 | 270.4 | 15 | 11751 |
| 4. Both Grooved, Opposite Twist | 6.1 | 0.62 | 824 | 1507 | >10.0 | 83.1 | 454.1 | ≦10 | 11351 |
| 5. Both Grooved, Same Twist | 6.4 | 0.75 | 785 | 1227 | 5.9 | 57.2 | 275.7 | 17 | 10639 |

*Testing for longitudinal matrix tensile strength was done with whole tubes on an Instron Model 1122 pull tester. The following settings were used:
1 crosshead speed of 200 mm/min.; and
2 initial distance between the jaws of 150 mm. Matrix tensile strength values are at 23° C.

EXAMPLE 3

Expansion Of Tube: Tip And Die With Four Helical Grooves

PTFE resin (Fluon CD-123 obtained from ICI Americas) was blended with 120 cc of "Isopar M" odorless solvent (produced by Exxon Corporation) per pound of PTFE, compressed into a tubular billet, heated to 60° C. and extruded into a 6 mm I. D. tube in a ram extruder having a reduction ratio of about 123:1 in cross-sectional area from billet to the extruded tube. The extruder tooling consisted of a tip with four helical grooves machined into it at a pitch angle of 45 degrees with respect to the longitudinal axis of the tip with a left hand twist and a die with four helical grooves machined into it at an angle of 45 degrees with respect to the longitudinal axis of the die with a right hand twist. The depth of grooves in the die is a continuous 0.51 mm. The grooves in the tip are this same depth at the upstream end and then taper gradually to zero depth at the exit end of the tip. This produced an extruded tube with ridges on the outer surface and a smooth inner surface.

This extruded tubing was then processed into a cylindrical tube of porous, expanded PTFE by the process described in U.S. Pat. No. 3,953,566. The stretch conditions were:
Temperature: approximately 300° C.
Stretch Ratio: 5:1 (400% increase in length)

whole tubes on an Instron Model 1122 pull tester. The following settings were used: (1) crosshead speed of 200 mm/min.; and (2) initial distance between the jaws of 150 mm. Matrix tensile strength values are at 23° C.

EXAMPLE 4

Expansion Of Tube: Tip And Die With Four Helical Grooves And Subsequent Smoothing Of External Surfaces Of Tubes A porous, expanded, amorphously locked PTFE tube was made from PTFE resin similar to that disclosed in U.S. Pat. Nos. 4,576,869; 4,016,345; and Re. 31,341. The method employed is as described in Example 2, except that 135 cc of "Isopar M" was blended with each pound of resin. The extruder tooling had grooves pitched in opposite directions, 45 degrees on the die and 135 degrees on the tip. After extrusion and prior to expansion, pressure was applied to the external surface of the tube by placing the tube on a mandrel and using roller means to smooth the ridges on the external surface of the tubes.

Another tube was made in the same manner but no smoothing of the external ridges was performed.

A third tube was similarly produced using smooth-walled tip and die. Certain physical properties of these tubes are summarized in Table 2.

TABLE 2

| Tube | Burst Pressure (psi) | Water Entry Pressure (psi) | Suture Retention Long. (g) | Suture Retention Transverse (g) | Fibril Length (microns) | Wall Thickness (mm) |
| --- | --- | --- | --- | --- | --- | --- |
| Smoothed External Surface | 74 | 7.1 | 2069 | 1243 | 16 | .076 |
| Ridged External Surface (No Smoothing) | 70 | 6.8 | 1678 | 1161 | 13 | .071 |
| Smooth-Walled Tip And Die | 46 | 5.0 | 1009 | 1084 | 22 | .081 |

EXAMPLE 5

Expansion Of Tube: Tip And Die With Four Helical Grooves

A porous, expanded, sintered PTFE tube was made from PTFE resin similar to that described for examples in U.S. Pat. Nos. 4,576,869; 4,016,345; and Re. 31,341. The method employed was similar to the method described above in Example 4 except for the following conditions:

Drying of Extruded Tubing: approximately 295° C. for 24 hours
Stretch Ratio: 11.2:1 (1020% increase in length)
Stretching Rate: approximately 47%/sec. (determined by dividing the percent change in length by the duration of the stretching operation)

The extruder tooling were of the same configuration as stated in Example 4.

Certain physical properties of this tube are summarized in Table 3. These are mean data calculated from several tubes.

TABLE 3

| Internal Diameter (mm) | Wall Thickness (mm) | Suture Retention Longitudinal (g) | Suture Retention Transverse (g) | Water Entry Pressure (psi) | Burst Pressure (psi) | Hoop Stress (psi) | Mean Fibril Length (microns) | Longitudinal Matrix Tensile Strength* (psi) |
|---|---|---|---|---|---|---|---|---|
| 5.9 | 0.64 | 1239 | 1228 | 4.9 | 62.0 | 319.8 | 76 | 11556 |

*Testing for longitudinal matrix tensile strength was done as described in Table 1 of Example 2.

While the invention has been disclosed herein in connection with certain embodiments and detailed descriptions, it will be clear to one skilled in the art that modifications or variations of such details can be made without deviating from the gist of this invention, and such modifications or variations are considered to be within the scope of the claims hereinbelow.

We claim:

1. An extruded and expanded tube of a porous material consisting essentially of polytetrafluoroethylene (PTFE) said tube having a longitudinal axis and tube wall having an inside radius and an outside radius, which PTFE material has a microsctructure characterized by elongated nodes, each node having a longitudinal axis and a transverse axis, which nodes are interconnected by fine fibrils, substantially all of said longitudinal axes of said nodes at at least one radial position within said tube wall being oriented at an angle between about 85 degrees and about 15 degrees with respect to said longitudinal axis of said tube.

2. The tube of claim 1 which has not been heated to a temperature above its crystalline melt point and which material has a crystallinity greater than about 95%.

3. The tube of claim 1 wherein substantially all of said longitudinal axes of said nodes which are located adjacent said inside radius of said tube are oriented at an angle between about 85 degrees and about 15 degrees with respect to said longitudinal axis of said tube, and substantially all of said longitudinal axes of said nodes which are located adjacent said outside radius of said tube are oriented at an angle between about 15 degrees and about 165 degrees with respect to said longitudinal axis of said tube.

4. The tube of claim 2 wherein said material has a matrix tensile strength in at least one direction above about 7,300 psi.

5. The tube of claim 1 wherein substantially all of said longitudinal axes of said nodes at at least one radial position within said tube wall are oriented at an angle of about 30 degrees to about 60 degrees with respect to said longitudinal axis of said tube.

6. The tube of claim 3 wherein substantially all of said longitudinal axes of said nodes which are located adjacent said inside radius of said tube are oriented at an angle of about 30 degrees to about 60 degrees with respect to said longitudinal axis of said tube, and substantially all of said longitudinal axes of said nodes which are located adjacent said outside radius of said tube are oriented at an angle of about 30 degrees to about 150 degrees with respect to said longitudinal axis of said tube.

7. A sheet produced by longitudinally slitting the tube of claim 1.

8. A sheet produced by rolling down the tube of claim 1.

9. An extruded and expanded tube of a porous material consisting essentially of polytetrafluoroethylene (PTFE) that has been heated to a temperature above the crystalline melt point, said tube having a longitudinal axis and tube wall having an inside radius and an outside radius, which PTFE material has a microstructure characterized by elongated nodes, each node having a longitudinal axis and a transverse axis, which nodes are interconnected by fine fibrils, substantially all of said longitudinal axes of said nodes at at least one radial position within said tube wall being oriented at an angle between about 85 degrees and about 15 degrees with respect to said longitudinal axis of said tube.

10. The tube of claim 8 wherein substantially all of said longitudinal axes of said nodes which are located adjacent said inside radius of said tube are oriented at an angle between about 85 degrees and about 15 degrees with respect to said longitudinal axis of said tube, and substantially all of said longitudinal axes of said nodes which are located adjacent said outside radius of said tube are oriented at an angle between about 15 degrees and about 165 degrees with respect to said longitudinal axis of said tube.

11. The tube of claim 9 wherein said material has a matrix tensile strength in at least one direction above 7300 psi.

12. The tube of claim 9 wherein said material has a matrix tensile strength in at least one direction above about 9,290 psi.

13. The tube of claim 9 wherein substantially all of said longitudinal axes of said nodes at at least one radial position within said tube wall are oriented at an angle of about 30 degrees to about 60 degrees with respect to said longitudinal axis of said tube.

14. The tube of claim 9 wherein substantially all of said longitudinal axes of said nodes which are located adjacent said inside radius of said tube are oriented at an angle of about 30 degrees to about 60 degrees with respect to said longitudinal axis of said tube, and substantially all of said longitudinal axes of said nodes which are located adjacent said outside radius of said tube are oriented at an angle of about 30 degrees to about 150 degrees with respect to said longitudinal axis of said tube.

15. A sheet produced by longitudinally slitting the tube of claim 9.

16. A sheet produced by rolling down the tube of claim 9.

17. The tube of claim 1 having a hoop strength exceeding 250 psi.

18. The tube of claim 17 having a hoop strength exceeding 450 psi.

19. The tube of claim 17 in use as an artificial vascular graft.

20. The tube of claim 9 having a hoop strength exceeding 250 psi.

21. The tube of claim 20 having a hoop strength exceeding 450 psi.

22. The tube of claim 20 in use as an artificial vascular graft.

* * * * *